United States Patent [19]

Morrison et al.

[11] Patent Number: 5,403,433
[45] Date of Patent: Apr. 4, 1995

[54] METHOD AND APPARATUS FOR MONITORING LAYER PROCESSING

[75] Inventors: Philip W. Morrison, Shaker Heights, Ohio; Peter R. Solomon, West Hartford, Conn.; Robert M. Carangelo, Glastonbury, Conn.; David G. Hamblen, East Hampton, Conn.

[73] Assignee: On-Line Technologies, Inc., East Hartford, Conn.

[21] Appl. No.: 116,295

[22] Filed: Sep. 3, 1993

Related U.S. Application Data

[63] Continuation-in-part of Ser. No. 913,377, Jul. 15, 1992, abandoned.

[51] Int. Cl.$^6$ ............................................. G01N 21/00
[52] U.S. Cl. .................................. 156/626; 427/8; 427/10; 204/192.13; 204/192.33; 356/381
[58] Field of Search ............... 156/626; 437/7, 8; 427/10, 8; 118/712; 204/192.13, 192.33, 298.03, 298.32; 356/381; 250/492.2

[56] References Cited

U.S. PATENT DOCUMENTS

| | | | |
|---|---|---|---|
| 2,844,032 | 7/1958 | Tandler et al. | 73/355 |
| 2,878,388 | 3/1959 | Bergson | 250/43.5 |
| 4,172,383 | 10/1979 | Iuchi | 73/355 |
| 4,332,833 | 6/1982 | Aspnes et al. | 427/8 |
| 4,415,402 | 1/1983 | Gelernt et al. | 156/626 |
| 4,417,822 | 11/1983 | Stein et al. | 374/129 |
| 4,465,382 | 8/1984 | Iuchi et al. | 374/9 |
| 4,493,745 | 1/1985 | Chen et al. | 156/626 |
| 4,590,574 | 5/1986 | Edmonds et al. | 364/498 |
| 4,652,755 | 3/1987 | Solomon et al. | 250/341 |
| 4,695,700 | 9/1987 | Provence et al. | 219/121 PD |
| 4,791,296 | 12/1988 | Carpio | 250/339 |
| 4,874,240 | 10/1989 | Watts et al. | 356/73 |
| 4,905,170 | 2/1990 | Forouhi et al. | 356/381 |
| 4,919,542 | 4/1990 | Nulman et al. | 374/9 |
| 4,974,182 | 11/1990 | Tank | 364/557 |
| 5,091,320 | 2/1992 | Aspnes et al. | 437/8 |
| 5,213,985 | 5/1993 | Sandroff et al. | 437/8 |
| 5,220,405 | 6/1993 | Barbee et al. | 356/357 |
| 5,229,303 | 7/1993 | Donnelly, Jr. et al. | 437/7 |
| 5,277,747 | 1/1994 | Aspnes | 156/626 |
| 5,294,289 | 3/1994 | Heinz et al. | 156/626 |
| 5,313,044 | 5/1994 | Massoud et al. | 219/121.85 |

OTHER PUBLICATIONS

Byffeteaut Desbat–"Thin–Film Optical Constants Determined From Infrared Reflectance and Transmittance Measurements" (Applied Spectroscopy) vol. 43, No. 6, 1989–pp. 1027–1032.

*Primary Examiner*—Thi Dang
*Attorney, Agent, or Firm*—Ira S. Dorman

[57] ABSTRACT

The method and apparatus of the invention permit in situ determinations to be made of the temperature and optical constants of a substrate surface that is being treated, by measurements of radiance, reflectance and transmittance. These determinations in turn provide, at any given instant during processing, compositional and other information, thereby affording highly effective feedback control of the processing conditions. The apparatus comprises an integrated, small and relatively inexpensive instrument for process monitoring.

27 Claims, 2 Drawing Sheets

METHOD AND APPARATUS FOR MONITORING LAYER PROCESSING

The U.S. Government has rights in this invention pursuant to Contracts Nos. DASG 60-89-C-0125, and F33615-91-C-1735, both awarded by the U.S. Department of Defense.

CROSS REFERENCE TO RELATED APPLICATION

This application is a continuation-in-part of application Ser. No. 07/913,377, filed Jul. 15, 1992, and now abandoned.

BACKGROUND OF THE INVENTION

There are many industrial processes in which materials are treated at elevated temperatures to alter their surface characteristics, and thereby their overall properties. It is of course advantageous to continuously monitor the surface of the material, and the ambient gas conditions, in situ during manufacture, to derive such information as will enable optimal process control. Particular advantage in this regard would inure from the provision of a single instrument that is capable of making non-contact measurements to obtain all relevant data simultaneously and on-line during production, and of means for employing the totality of the information obtained so as to achieve improved accuracy and to realize the self-evident benefits that are attendant thereto.

An especially notable application for such process-monitoring technology lies in the semiconductor industry, where the need exists for reliably determining, and thence controlling, the physical and electronic properties of thin film structures in the course of production. The required information is known to be contained in the optical film constants, from which knowledge rather crude empirical correlations have been developed that relate film properties to, for example, the index of refraction ($n_\infty$) in the visible range. That parameter is typically measured however at a wavelength that is remote from the absorption features that correlate directly its film composition (e.g., by reflectance or ellipometry), and is therefore of only limited value.

The determination of temperature, and certain related properties, by making non-contact measurements is well known in the art. Thus, in U.S. Pat. No. 4,172,383, Iuchi discloses a device for measuring the temperature and emissivity of a heated, specular reflecting material. U.S. Pat. No. 4,417,822, to Stein et. al., provides a laser radiometer. In U.S. Pat. No. 4,456,382, Iuchi et. al. disclose a device for measuring the temperature and emissivity of a heated material knowing the temperatures of both the ambient surroundings and also the furnace. In accordance with Tank U.S. Pat. No. 4,974,182, the temperature and emissivity of an object are obtained by making radiance measurements from the object at multiple frequencies and at different temperatures, while it is either heated or cooled, so as to eliminate the influences of the temperature and absorption characteristics of the surrounding ambient. U.S. Pat. No. 4,919,542, to Nulman et. al., teaches a technique by which the emissivity and temperature of an object having zero transmission are determined by measurements of radiance and reflectivity, the ambient radiation for a selected range of processing temperatures being accounted for by making calibration measurements in which the true sample temperature is determined by, for example, contact thermometry.

The determination of layer thickness by optical means is also described in the art. In U.S. Pat. No. 4,555,767, to Case et. al., the infrared reflectivity of an object is measured to determine the thickness of an epilayer of known composition; this is done by comparing the measured reflectance to values of theoretical reflectance determined for different thickness of an epilayer and the substrate.

The prior art also provides optical techniques for determining the composition of a material. In a publication by Buffeteau and Desbat, entitled "Thin-Film Optical Constants Determined from Infrared Reflectance and Transmittance Measurements" (*Applied Spectroscopy*, Vol. 43, No. 6, 1989, pages 1027 through 1032), the authors describe a general method, based upon reflectance and transmittance measurements, for the determination of the optical constants, $n(v)$ and $k(v)$, of thin films deposited upon any substrate, transparent or not. The corresponding computer program involves three main parts: (1) a matrix formalism to compute reflection and transmission coefficients of multilayered systems; (2) an iterative Newton-Raphson method to estimate the optical constants by comparison of the calculated and experimental values; and (3) a fast Kramers-Kronig transform to improve the accuracy of calculating the refractive index. It is disclosed that the first part of the program can be used independently to simulate reflection and transmission spectra of any multilayered system using various experimental conditions.

In U.S. Pat. No. 4,791,296, to Carpio, the measurement of infrared transmission is employed in a dual beam apparatus to determine the phosphorous concentration in PSG and BPSG films. This is accomplished by comparison of a transmission measurement, made through a substrate upon which a film is deposited, to a transmission measurement of the substrate alone; the measured transmittance difference is compared to calibration curves. The American Society for Testing Materials has issued standards to measure carbon (Standard No. F-121-76) and oxygen (Standard No. F-123-74) (1) using IR absorption spectroscopy. In U.S. Pat. No. 4,590,574, to Edmonds, the oxygen in wafers having one rough surface is measured by employing the shape of an IR transmission to determine roughness, and to thereby correct the measurement of the oxygen or carbon absorption peaks for the affect of the rough surface. The dielectric function of a surface, obtained by ellipsometry over the range of frequencies 1.5 eV to 6 eV, is employed by Aspnes et. al. in U.S. Pat. No. 4,332,833 to determine the microstructure of the material.

Determination of the end point of a plasma etch process, applied to a surface, has been accomplished by noting changes in the character of the ambient above the surface. Thus, in U.S. Pat. No. 4,455,402, to Gelernt et. al., a spectrophotomatic observation of the plasma is employed using a single detector; in U.S. Pat. No. 4,695,700, to Provence et. al., two detectors are utilized; and in U.S. Pat. No. 4,493,745, to Chen et. al., a simulation is employed to predict the etch end point from a measured part of the optical emission spectroscopy.

A gas temperature measurement system, operating upon absorbed and emitted radiation, is described in Tandler et. al., U.S. Pat. No. 2,844,032. In U.S. Pat. No. 2,878,388, Bergson discloses a system for analyzing gases by measuring the absorption of radiant energy.

It is known that laser interferometry can be employed to monitor etch depth in a plasma reactor, using a method that relies upon the time dependence of the diffraction from a patterned substrate to determine the depth of etching as a function of time. Also, in situ ellipsometry has previously been performed on dielectric layers to measure thickness, and light scattering has been utilized to measure film thickness in a MOCVD reactor. Infrared interference techniques have been successfully applied to epitaxial GaAs layers in making film thickness measurements.

Mass spectrometry is known to be a highly sensitive technique for measuring ion concentrations and energy distributions at a surface. Optical emission spectroscopy uses visible radiation emitted by the plasma as a diagnostic, and laser-induced fluorescence can be used to yield relative concentration, and some temperature, information.

Dispersive IR instruments have been employed to measure gas phase absorbances outside of a plasma processing zone, and IR lasers have been proposed for making in situ measurements. In limited instances, in situ Fourier Transform Infrared (FTIR) spectroscopy has been applied to plasma processing; e.g., to record high resolution spectra of a $SiH_4$ plasma in both emission and absorption, and to study the plasma etching of $SiO_2$ by $CF_4$. Spectrometers have also been employed to investigate $N_2O$ plasmas; in situ studies have been made on films of amorphous hydrogenated silicon, using a dispersive IR spectrometer and polarizing the IR to remove gas absorptions; and several authors have reported making in situ IR measurements on films of a-Si:N:H, a-Si:F(H), and $SiO_2$.

Despite the prior art exemplified by the foregoing, the need exists for a fast and accurate method, and a unitary apparatus for performing the same, by and with which a multiplicity of characteristics of a substrate surface undergoing modification can be determined, in situ and simultaneously, for effective control of the processing conditions.

SUMMARY OF THE INVENTION

Accordingly, the broad objects of the present invention are to provide a novel method that is capable of satisfying the foregoing need, and to provide a novel, unitary apparatus for carrying out such a method. Related objects are to provide such a method and apparatus in and by which effective control of processing conditions can readily be afforded.

It has now been found that certain of the foregoing and related objects of the invention are attained by the provision of a method for the treatment and in situ analysis of an article during processing, comprising the steps:

(a) providing a substrate having a surface;

(b) treating at least a portion of the surface for a certain period of time to effect modification thereof, and carrying out the following steps in connection with the surface portion, as so modified;

(c) substantially continuously throughout the treatment period causing electromagnetic radiation of frequencies v throughout a selected spectral range, to impinge upon the surface portion at a selected angle of incidence;

(d) substantially continuously throughout the period measuring, at substantially the specular angle, spectral reflectance of the impinging radiation from the surface portion, as a function of frequency;

(e) substantially continuously throughout the period measuring the radiance of the surface portion, at least at one selected wavelength;

(f) determining, from the reflectance and radiance data obtained in steps (d) and (e), the temperature of the surface portion at selected instants during the treatment period; and (g) determining optical constants for the surface portion at the same selected instants by (1) selecting values for the optical constants utilizing a selection scheme in which the imaginary component of the optical constant expression is represented by a selected number s of oscillators spaced across at least a portion of the selected spectral range of impinging radiation, s having a value of at least two; (2) calculating reflectance based upon the angle of incidence, the selected values for the optical constants, and the thickness of any film of material that may be developed upon the substrate surface in step (b); (3) comparing the calculated reflectance to the value of reflectance measured in step (d); and (4) iteratively adjusting the selected values of optical constants and comparing the calculated reflectance and measured reflectance value until the calculated reflectance substantially equals the measured value. Desirably, the oscillators will be spaced at equal intervals, and the value of s will be at least ten.

As will be appreciated, the modification effected by the treating step (b) may comprise the development of a film of material upon the substrate surface portion; alternatively, it may comprise the removal of material therefrom. In most embodiments the selected spectral region of irradiation and measurement will lie in the infrared range (i.e., encompassing wavenumbers of 10,000 to 200 $cm^{-1}$), and the method will usually include a step (h) of measuring spectral transmittance of the impinging radiation through the surface portion, unless transmission of that radiation therethrough is known to be zero. Preferably, the method will include the additional steps of identifying features of the reflectance measured in step (d) that are attributable to absorbance of radiation by ambient gases, and subtracting those features from the measured reflectance, and of determining the temperature of the ambient gases from the reflectance measurement. Most desirably, spectral radiance will be measured in step (e), and the method will serve to simultaneously determine, at selected instants, the spectral emittance, temperature, thickness, and composition of the surface portion, as modified, as well as the temperature and composition of ambient gases. As a practical matter, the method will generally include an ultimate step of controlling the treating step (b), based upon the temperature and optical constants determined, so as to effectively produce an article having desired properties.

The temperature T of the substrate surface portion will advantageously be determined by the steps of: determining the reflectance $R_o$ at the "one" selected wavelength measured in step (e); determining any transmittance $t_o$ of the one selected wavelength, measured in step (h); using the values so determined to determine the fraction $a_o$ of radiation, at the one selected wavelength, that is absorbed by the surface portion, by application of the equation:

$$a_o = 1 - R_o - t_o,$$

and thereby determining the spectral emittance $e_o$ of the surface portion at the one selected wavelength, by the equation:

$$e_o = a_o;  \text{and}$$

matching the quantity $E_o/e_o$ to the spectral rdiance $B_o(T)$ of a theoretical black body at the selected wavelength, to determine T in accordance with the relationship:

$$E_o/e_o = B_o(T),$$

wherein $E_o$ represents the one selected wavelenght radiance measured in step (e). In those instances in which spectral radiance $E_\nu$ is measured in step (e), the spectral emittance $e_\nu$ of the surface portion, as so modified, may additionally be determined over the selected spectral range, by either of the relationships:

$$a_\nu = 1 - R_\nu - t_\nu \text{l and } e_\nu = a_\nu; \quad (1)$$

or $$e_\nu = E_\nu/B_\nu(T), \quad (2)$$

wherein $R_\nu$ and $t_\nu$ represent the spectral reflectance and transmittance measured, respectively, in steps (d) and (h), and wherein $B_\nu(T)$ is the spectral radiance of a theoretical black body at temperature T over the selected spectral range.

The optical constants determined in step (g) of the method will desirably be the complex dielectric function, and the real and imaginary components thereof, represented respectively by the terms of the equation $$\epsilon(\nu) = \epsilon_r(\nu) + i\epsilon_i(\nu).$$

In the preferred embodiments, those constants will be determined by application of the equation:

$$\epsilon(\nu) = \epsilon_\infty + \Sigma_j \frac{v_{pj}^2 f_j}{v_j^2 - v^2 - ig_j v},$$

and by minimizing the sum, over all values of k, of the expression $[R_{data}(V_k) - R(v_k)]^2$, with respect to $A_j$. In the foregoing: $\epsilon(\nu)$ is the complex dielectric function; $\epsilon_{28}$ is the dielectric constant in the visible region of the spectrum; j represents an integer having a value from 1 to s; in each of the summed oscillators of index j, constituting the imaginary part of the dielectric function $v_p^2$ is the square of the plasma frequency, equal to $Ne^2/m\epsilon_o c^2$, in which N is the number density of absorbers, e is the charge on an electron, m is the mass of an electron, $\epsilon_o$ is the permittivity, and c is the speed of light; $v_j$ is the resonant absorption frequency; $f_j$ is the oscillator strength; $g_j$ is the transition probability; $A_j$ represents oscillator peak amplitude equal to $v_{pj}^2 f_j/g_j v_j$; t is the number of data points to fit; k represents an integer having a value from 1 to t; $R_{data}$ is the measured value of reflectance; and the calculated reflectance R is simulated from the $A_j$ value. In this embodiment of the method, the sum of the expression set forth may be minimized by the iterative solution method represented by the equation:

$$\begin{bmatrix} \delta R/\delta A_1(v_1) & \delta R/\delta A_2(v_1) & \ldots & \delta R/\delta A_s(v_1) \\ \delta R/\delta A_1(v_2) & \delta R/\delta A_2(v_2) & \ldots & \delta R/\delta A_s(v_1) \\ \vdots & & & \\ \delta R/\delta A_1(v_t) & \delta R/\delta A_2(v_t) & \ldots & \delta R/\delta A_s(v_t) \end{bmatrix} \begin{bmatrix} \Delta A_1 \\ \Delta A_2 \\ \Delta A_s \end{bmatrix} =$$

$$= \begin{bmatrix} R_{data}(v_1) - R(v_1) \\ R_{data}(v_2) - R(v_2) \\ \vdots \\ R_{data}(v_t) - R(v_t) \end{bmatrix}$$

wherein $\Delta A$ is an estimated correction to A.

Other objects of the invention are attained by the provision of apparatus for the in situ analysis of an article during processing, comprising:

(a) means for producing electromagnetic radiation of frequencies v throughout a selected spectral range, and for causing such radiation to impinge at a selected angle of incidence upon the surface of a substrate supported in a position proximate the apparatus;

(b) means for continuously measuring, as a function of frequency, specular reflectance of such impinging radiation from the surface of the substrate so supported, and for storing data so obtained;

(c) means for continuously measuring, at least at one selected wavelength, the radiance of the surface of the substrate so supported, and for storing data so obtained; and (d) electronic data processing means programmed and operatively connected for processing reflectance and radiance data obtained by the means for measuring to determine, at any instant, the temperature of and the optical constants for the substrate surface, those properties being determined in accordance with the methodology herein described.

In preferred embodiments of the apparatus, the means for producing, both of the means for measuring, and the data processing means, will all comprise a single instrument, most desirably including an FT-IR spectrometer. The data processing means may be programmed to determine the complex dielectric function of the substrate surface, and the real and imaginary components thereof, and it will preferably do so by application of the equation:

$$\epsilon(\nu) = \epsilon_\infty + \Sigma_j \frac{v_{pj}^2 f_j}{v_j^2 - v^2 - ig_j v}.$$

Most desirably, the data processing means will be programmed to identify features of the measured reflectance that are attributable to absorbance of radiation by ambient gases, and for subtracting the value of such features from the measured radiance values, as well as being programmed to determine the temperature of the ambient gases from the measured reflectance.

Generally, the apparatus will additionally include means (e) for continuously measuring, as a function of frequency, specular transmittance of the impinging radiation through the substrate so supported, and for storing data so obtained. The data processing means may be programmed to determine the temperature T of the substrate surface by determining $e_o$ and $E_o$, and by matching black body spectral radiance thereto, as described. It may also may be programmed to determine the spectral emittance $e_v$ of the substrate surface, also in the manner set forth above.

In particularly preferred embodiments, the data processing means will programmed and operatively connected for generating an electrical signal that is indicative of the determined temperature and optical constants of the substrate surface. The apparatus may additionally include controllable means for treating the surface of a substrate for effecting modification thereof, as well as means for controlling the means for treating so as to vary the conditions produced. With the means for controlling operatively connected to the data processing means, and being responsive to the electrical signal generated thereby, feedback control of the processing conditions is afforded.

BRIEF DESCRIPTION OF THE DRAWINGS

FIGS. 2(a), 2(b) and 2(c) are curves showing the deconvolution of the dielectric function for a simulated $SiO_2$ film on silicon, FIG. 2(a) showing the simulated reflectance for the film, together with the error between the simulation and the deconvolution.

DETAILED DESCRIPTION OF THE ILLUSTRATED EMBODIMENT

Figure 1:
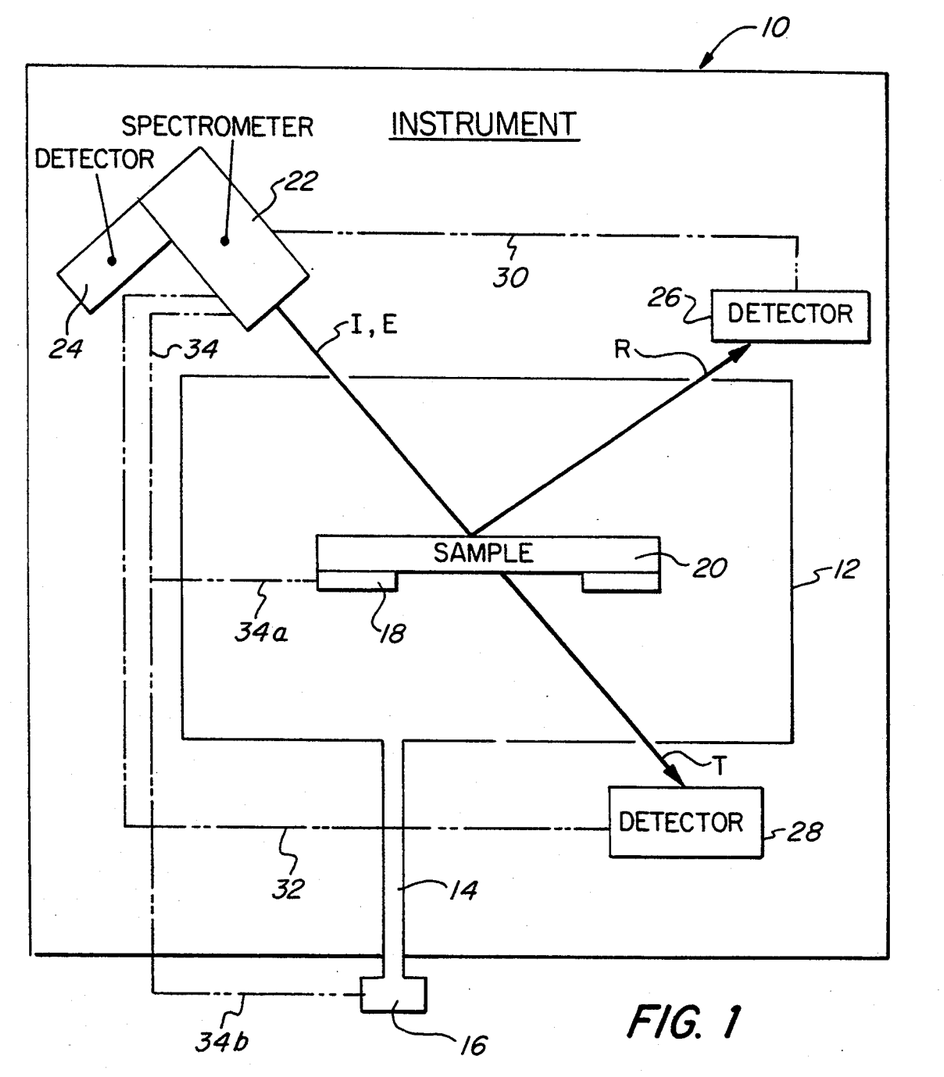
FIG. 1 is a diagrammatic view of a unitary instrument embodying the apparatus of the invention.

Turning in detail to FIG. 1 of the drawings, therein diagrammatically illustrated is an instrument embodying the present invention, generally designated by the numeral 10. Defined within the instrument 10 is a sample compartment 12, into which leads a conduit 14 connected to a valved gas supply 16. An electrically-heated support 18 is provided within the chamber 12, and serves to support the sample or substrate 20 being monitored by the instrument while processing is performed thereon.

The instrument 10 also includes an FT-IR spectrometer (including a computer, usual optics, interferometer, and all of the other conventional components thereof), with which is associated (and operatively connected) a detector 24 for measuring the emissivity of the surface of the sample 20. Also associated with the spectrometer 22 is a reflectance detector 26 and a transmittance detector 28, operatively connected to the spectrometer by lines 30 and 32, respectively. A line 34 leads from the spectrometer to the heating element of the sample support 18 and the valve of the gas supply 16, through branches 34a and 34b, respectively, operatively connecting them for control by the spectrometer 22. As indicated by the letters I and E, the incident radiation impinging upon the sample 20, and the radiation emitted thereby (radiance), follow the same path from and to the spectrometer 22. Reflected radiation follows path R to the detector 26, and transmitted radiation follows path T to the detector 28. The manner in which the several beams are employed for determining the properties of the sample 20 and the ambient gas, and for utilizing the data so obtained for feedback control of power to the heated support 18 and gas flow from the supply 16, are described in detail herein.

It will be appreciated that the method of the invention can be utilized for the on-line analysis and fabrication of a wide variety of articles; it is however applied with particular advantage in the production of semiconductor devices. As previously mentioned, the process can involve not only the deposition of a material or materials upon the surface of a substrate, to produce a film or layer-like deposit, but also the treatment of a surface to selectively remove the material thereof (e.g., by etching or ablation), or to effect its chemical modification or conversion. Generally, but not necessarily, processing will take place in a chamber, such as for the confinement of a plasma in semiconductor manufacture, for chemical-vapor deposition (CVD), for thermal annealing, etc. The substrate employed, and/or a film or deposit produced thereon, will preferably be opaque to the probe radiation, and most desirably the surface will be specularly reflecting. Nevertheless, transmitting surface/substrate combinations may successfully be monitored in accordance with the invention, and specularity is not essential to the achievement of good characterizations of surface properties; in all instances, however, specularity will be assumed, and reflectance measurements will be made at or about the specular angle.

Operating conditions, and the regulation and modification thereof, will depend of course upon the nature of the treatment to which the substrate is subjected in the process, and upon the properties that the product, and its constituent layers or films, are to have. The many variables that might be controlled will be evident to those skilled in the art; typically however they include the power supply to a substrate heater, a plasma power supply, the flow, composition, pressure, and temperature of a gaseous reactant stream, and of course process termination. These conditions will be maintained, varied or implemented depending upon one or more of a number of parameters; i.e., the determined substrate surface temperature and composition, film thickness, ambient gas composition and temperature, etc. It might also be mentioned that any treatment involved in the practice of the invention will usually be carried out at a temperature in the range 0° to 1000° C., and that when films are produced their thicknesses will generally range to about 100 $\mu$m.

Although an FT-IR spectrometer will preferably comprise the apparatus of the invention, and be employed in carrying out the method hereof, other means may be used for obtaining the relevant data; apparatus that generates and measures polarized radiation may be employed to detect changes in polarization, if so desired, IR fiber-optic means may be utilized, etc. Irradiation, and reflectance, transmittance, and radiance measurements, will usually be made at wavenumbers in the range 400 to 6500 $cm^{-1}$, but wavelengths in other spectral regions may be used in appropriate circumstances.

It will be appreciated that a primary benefit of the instant invention resides in the ability that it affords for simultaneously determining, at any given time, a multiplicity of the characterizing properties of the monitored surface and the ambient gas; e.g., surface temperature, surface composition (advantageously as a function of distance from a reference surface), film thickness, spectral emittance, ambient gas composition and temperature, etc. The starting parameters of the substrate employed may either be of known values or determined as a first step of the process. In carrying out the process, all calculations of surface parameters will generally be made using spectra corrected for ambient gas absorption and emission bands by base-line subtraction. Also, the apparatus employed will normally incorporate means for obtaining reference spectra for reflectance, transmittance, radiance, and radiance background, as by enabling replacement of the sample by a gold mirror, displacement of the sample out of the irradiation path, disposing a black-body standard at the position of the specular reflectance detector, and the like; an external reference mirror may also be utilized, as may computer-stored reference spectra. Although very good results can usually be achieved by making measurements at or about the spectral angle, as previously noted, in some instances it may be preferred to provide in the instrument a series of apertures, and automatic shutters, for measuring reflectance at several angles so as to determine any non-spectral portion of the reflected radiation.

Essential to the satisfactory characterization of the surface of any substrate, or of any film or deposit produced thereupon, is the determination of its temperature. Techniques for doing so utilizing in situ reflection and emission spectroscopy have previously been developed, and are fully described in co-pending application Ser. No. 07/512,422, now U.S. Pat. No. 5,239,488. In accordance therewith, and as discussed above, radiance and reflectance (together with transmittance, unless the material is known to be opaque to the radiation employed) are measured to determine a single-wavelength emittance of the probed surface, which is in turn employed to determine the temperature of the surface, by a Planck function (black body) matching technique.

In many instances (particularly those in which a dielectric material is involved), reflectance will be zero at least at one (Christiansen effect) wavenumber. Radiance at the Christiansen effect wavenumber can then be utilized to readily determine the temperature; this concept, and its implementation, are described more fully in Morrison et. al. U.S. Pat. No. 4,985,858.

As noted above, empirical relationships are already known by which film characteristics can be correlated, to at least some degree, to measurable optical properties. A more effective approach is however provided by the present invention, which enables examination of the optical spectrum closer to absorption resonances in the mid-infrared range, such resonances being directly related to the chemical bonds in the material. Thus, given the thickness and the optical constants (as functions of wavenumber) for each film or layer (discrete or not) in a multilayer structure, or "stack," and the angle of incidence of the probe radiation, the reflectance (and transmittance) of the structure can be calculated.

The optical constants of interest may be in the form of the complex refractive index [m (v)=n (v)+ik (v)], or the complex dielectric function [$\epsilon(v) = \epsilon_r(v) + i\epsilon_i(v)$], where n is the refractive index and k is the absorption index, and $\epsilon_r$ and $i\epsilon_i$ are the real and imaginary components of $\epsilon(v)$. It will be appreciated that $m^2(v)$ is equal to $\epsilon(v)$, and that the analysis is based upon the assumption that the substrate is either infinitely thick or highly scattering, to preclude reflectance from its back surface, but this is not necessarily true in all cases.

The optical constants are, in either case, determined in accordance with the invention by deconvolution (or, more properly, inversion) of measured reflectance; the methodology entails the application of the quantum theory that relates the IR values of e(v) to fundamental parameters, as by the formula:

$$\epsilon = \epsilon_\infty + \Sigma_i \frac{v_{pj}^2 f_j}{v_j^2 - v^2 - ig_j v}$$

the terms of which have hereinbefore been defined. The equation is mathematically equivalent to the Lorentzian formalism, the imaginary part of which has a peak of amplitude $A_j = v_{pj}^2 f_j / g_j v_j$, and an approximately width of $g_j$. The real part is related to the imaginary part through the Kramers-Kronig relation, and has the typical dispersion shape; similar shapes hold for n(v) and k(v). Different materials have a number of superimposed Lorentzians, of varying amplitude, width, and resonant frequencies yielding a distinctive shape for $i\epsilon_i(v)$. Thus, such parameters are directly related to chemical bond information, and the area under each peak is directly related to the number of absorbers of that kind. It should perhaps be mentioned that certain materials, which do not conform to the Lorentzian model, can nevertheless be characterized by application of the techniques herein described.

From the above-cited article by Buffeteau and Desbat, it is known that deconvolution at each wavenumber is possible if the reflectance and transmittance of a film can be measured. The Buffeteau and Desbat method fails however if only the reflectance is available; and although in principle the Kramers-Kronig transform can be used to relate the optical constants to one another, doing so requires the full spectrum and cannot be implemented on a wavenumber-by-wavenumber basis. Assumptions as to the shape of the imaginary component of the dielectric function have been employed in an effort to obtain the required information, but such assumptions are inapplicable to many materials of interest.

The present methodology simplifies the problem of searching complex and ill-defined parameter spaces, through application of algorithms that are unstable, by fixing the number of oscillators employed and placing them, preferably at equal intervals, across the spectrum of interest. Typically, a peak will be placed at every 15 cm$^{-1}$ between 500 and 2500 cm$^{-1}$, giving them a width (g) equal to 30 cm$^{-1}$. Thus, each peak so designated will have the same width but an unknown amplitude; and as long as the spectrum contains no features less than $g_j$ in width, the sum of the several peaks can adequately recreate an $i\epsilon_i$ feature wider than $g_j$. The formalism therefore reduces to the problem of searching only the $A_j$ space.

It should be noted that the foregoing method accounts for the absorption bands of the film, but for neither the $\epsilon_\infty$ in the visible ($n_\infty^2$), nor for the thickness z. Estimates of those parameters can be made however using the transparent region (v greater than 2000 cm$^{-1}$) of the film or surface, at which region the interference fringes dominate the spectrum. As the zeroth approximation, it may be assumed that $n_\infty$ is constant, with $\epsilon_\infty$ and z being varied until the thus simulated fringes roughly match the data. It should also be noted that there will be more than one pair of $\epsilon_\infty$ and z that will match the data, but that knowledge of a very rough estimate of either variable will allow convergence to reliable values of $\epsilon_\infty$ and z.

After the foregoing parameters have been established, a multivariable nonlinear fit can be solved to determine the amplitudes $A_j$; the solution equation has hereinabove been set forth and defined! In application thereof, the derivatives in the correlation matrix, and reflectance R, are calculated numerically using the film simulation method of the cited Buffeteau and Desbat article. Once the absorption region has been deconvoluted the values of $\epsilon_\infty$ and z can be reestimated, and the sequence repeated; typically, once the solution equation has converged an excellent solution can be achieved with but a single reestimation.

Film thicknesses are evidenced by the character of large absorption features present in the reflectance spectra, which are indicative of destructive interference. Using the method of Buffeteau and Desbat to calculate reflectance, an iterative approach to determining thickness is also afforded.

EXAMPLE ONE

Figure 2A:
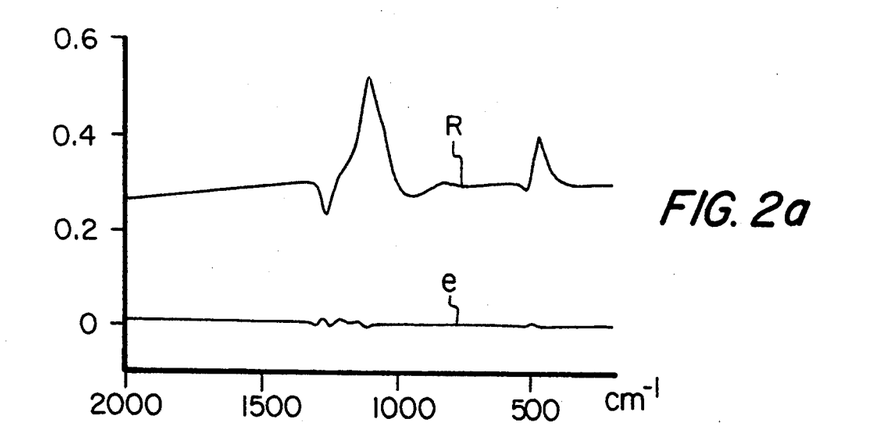
Figure 2B:
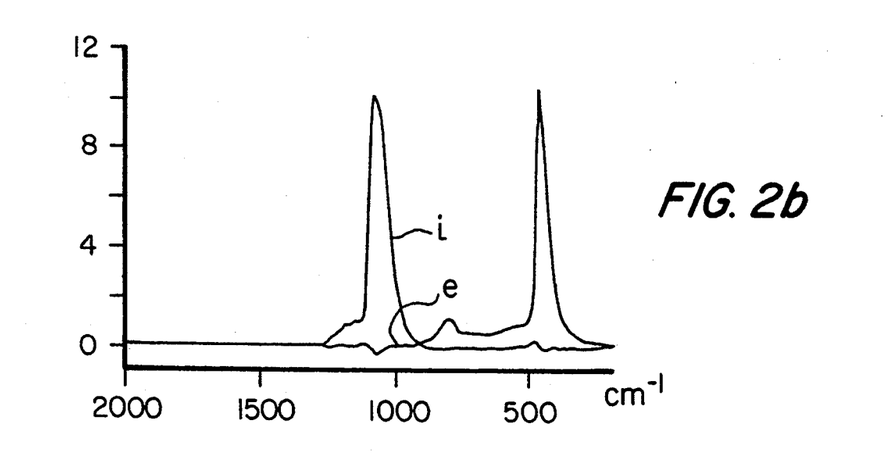
FIG. 2(b) showing literature values for the imaginary part of the dielectric function of $SiO_2$, together with the error between the literature and the experimental deconvoluted values.
Figure 2C:
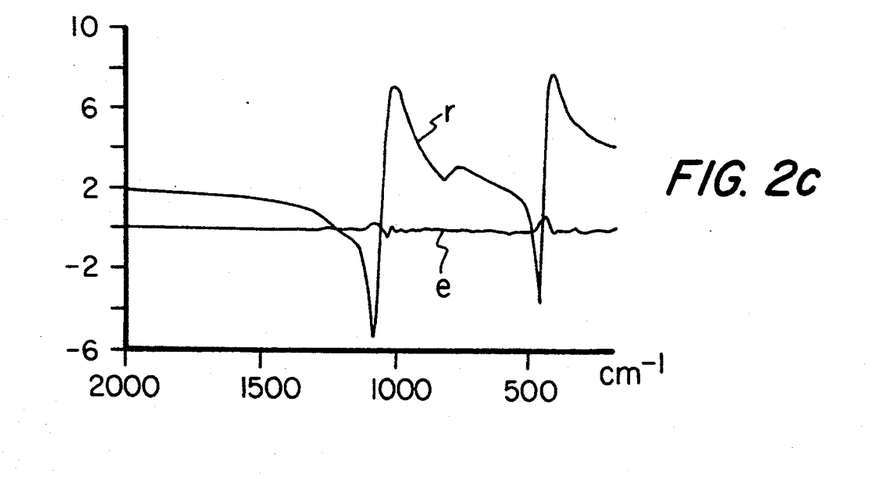
FIG. 2(c) showing literature values for the real part of the dielectric function of $SiO_2$, together with the error between the literature values and the experimental deconvoluted values.

The efficacy of the method is demonstrated by calculating, from the known optical constants of $SiO_2$, the reflectance of a 0.389 μm film on Si, deconvoluting the spectrum to yield estimates of $i\epsilon_i$ and $\epsilon_r$, and comparing them to the starting values. Appended FIG. 2a shows the reflectance R of the $SiO_2$/Si multilayer in the region below 2000 $cm^{-1}$, and FIGS. 2b and 2c depict the imaginary i and real r parts of $\epsilon(v)$ used to simulate FIG. 2a. A crude fit to the interference fringes yields $\epsilon_{28} \approx 2.05$ and z=0.39. Given these initial guesses, the deconvolution of the $A_j$ produces results that match the data very closely after adjusting $\epsilon_\infty$ to 2.113 and z=0.39. For comparison, the errors e calculated by subtracting the deconvoluted values from the starting values also appear in the Figures. Thus, deconvolution converges on an answer, as shown in FIG. 2a, and it converges to the correct answer, shown in FIGS. 2b and 2c. Although not graphically depicted, the fit is excellent throughout the entire spectrum. The deconvolution is, furthermore, insensitive to the initial guess; the solution is very stable, and it converges in less than 20 iterations of the solution equation.

As will be appreciated from the description provided herein, optical monitoring of the surface during processing is relatively straightforward if the gases used to alter the surface (e.g., by deposition, etching, phase change, doping, etc.) are either non-absorbing or have absorption bands that do not coincide with the absorption features of the substrate surface. However, the gas bands frequently do overlap the film bands, adding linearly in the spectrum, and will in many instances overwhelm the absorption features of the surface being monitored.

This problem can be averted by using characteristics of the absorptions to identify the gases and to selectively remove them from the combined spectrum. Under many circumstances the gas absorption spectrum will consist of a variety of rotational "lines,"0 which are less than 1 $cm^{-1}$ wide and are spaced 0.1 to 5 $cm^{-1}$ apart; furthermore, a single gas can have multiple absorption bands located in different parts of the spectrum. In contrast, the absorptions of a solid surface are tens of $cm^{-1}$ wide, and are fairly uniquely positioned in the spectrum. Because the gas rotational lines are so much narrower than are the bands attributable to the solid, a portion of a reference spectrum indicative of the gas can be subtracted from the combined spectrum until the distinctive, narrow features disappear. Similarly, if a reference spectrum is subtracted until an isolated gas band disappears, all of the other absorption bands due to the presence of the ambient gases should also disappear, with the remainder of the spectrum being due to the film characteristics plus any gas species not accounted for. Selective application of the subtraction methodology can therefore be applied to remove those remaining gas absorptions in turn, until only the broad band absorptions of the solid remain. The temperature $T_g$ of the ambient gas can be determined by measuring, as a function of frequency, the transmittance t(v) and radiance R(v) through and of the gas, and by determining the Planck function $B_v(T)$ that equals the quantity $R(v)/1-t(v)$.

Thus, it can be seen that the present invention provides a novel, fast and accurate method, and a novel unitary apparatus for performing the same, by and with which a multiplicity of characteristics of a substrate surface undergoing modification can be determined, in situ and simultaneously. The invention also provides such a method and apparatus in and by which effective control of processing conditions can readily be afforded.

Having thus described the invention, what is claimed is:

1. A method for the treatment and in situ analysis of an article during processing, comprising the steps:
(a) providing a substrate having a surface;
(b) treating at least a portion of said surface for a certain period of time to effect modification thereof, optionally by developing a film of material thereon, and carrying out the following steps in connection with said surface portion, as so modified;
(c) substantially continuously throughout said period causing electromagnetic radiation of frequencies v throughout a selected spectral range to impinge upon said surface portion at a selected angle of incidence;
(d) substantially continuously throughout said period measuring, at substantially the specular angle, spectral reflectance of said radiation from said surface portion, as a function of frequency;
(e) substantially continuously throughout said period measuring the radiance of said surface portion at least at one selected wavelength;
(f) determining, from the reflectance and radiance data obtained in said steps (d) and (e), the temperature T of said surface portion at selected instants during said period of time; and
(g) determining optical constants for said surface portion at said instants by (1) selecting values for said optical constants utilizing a selection scheme in which the imaginary component of the optical constant expression is represented by a selected number s of oscillators spaced across at least a portion of said selected spectral range, s having a value of at least two; (2) calculating reflectance based upon said angle of incidence, said selected values for said optical constants, and the thickness of any film of material that may be developed upon said substrate surface in said step (b); (3) comparing said calculated reflectance to the value of said reflectance measured in said step (d); and (4) iteratively adjusting said selected values of optical constants and comparing said calculated reflectance and measured reflectance value until said calculated reflectance substantially equals said measured value.

2. The method of claim 1 wherein said modification effected by said treating step (b) comprises developing a film of material upon said substrate surface portion.

3. The method of claim 1 wherein said modification effected by said treating step (b) comprises removing a material from said substrate surface portion.

4. The method of claim 1 wherein said selected spectral range lies in the infrared range.

5. The method of claim 1 including the additional step (h) of measuring spectral transmittance of said radiation through said surface portion, unless transmission of said radiation therethrough is known to be zero.

6. The method of claim 5 wherein said temperature T is determined by determining the reflectance $R_o$ at said one selected wavelength, measured in said step (d); determining the transmittance $t_o$ of said one selected wavelength, measured in said step (h); using the values so determined to determine the fraction $a_o$ of said radiation, at said one selected wavelength, that is absorbed by said surface portion, by application of the equation:

$$a_o = 1 - R_o - t_o,$$

and thereby determining the spectral emittance $e_o$ of said surface portion at said one selected wavelength, by the equation:

$$e_o = a_o; \text{ and}$$

matching the quantity $E_o/e_o$ to the spectral radiance $B_o(T)$ of a theoretical black body at said selected wavelength, to determine T in accordance with the relationship:

$$E_o/e_o = B_o(T),$$

wherein $E_o$ represents said one selected wavelength radiance measured in said step (e).

7. The method of claim 6 wherein spectral radiance $E_\nu$ is measured in said step (e), and wherein, in said step (f), the spectral emittance $e_\nu$ of said surface portion, as so modified, is additionally determined over said selected spectral range, by either of the relationships:

$$a_\nu = 1 - R_\nu - t_\nu; \text{ and } e_\nu = a_\nu; \quad (1)$$

or $$e_\nu = E_\nu / B_\nu(T), \quad (2)$$

wherein $a_\nu$ represents spectral absorbance, and $R_\nu$ and $t_\nu$ represent the spectral reflectance and transmittance measured, respectively, in said steps (d) and (h), and wherein $B_\nu(T)$ is the spectral radiance of a theoretical black body at temperature T over said selected spectral range.

8. The method of claim 4 wherein said optical constants determined in said step (g) are the complex dielectric function and the real and imaginary components thereof, represented respectively by the terms of the equation $$\epsilon(\nu) = \epsilon_r(\nu) + i\epsilon_i(\nu).$$

9. The method of claim 8 wherein said optical constants are determined by application of the equation:

$$\epsilon(\nu) = \epsilon_\infty + \Sigma_j \frac{\nu_{pj}^2 f_j}{\nu_j^2 - \nu^2 - ig_j\nu}$$

wherein $\epsilon(\nu)$ is the complex dielectric function; wherein $\epsilon_\infty$ is the dielectric constant in the visible region of the spectrum; wherein j represents integers from 1 to s; wherein, in each of the summed oscillators of index j, constituting the imaginary part of the dielectric function, $\nu_p^2$ is the square of the plasma frequency, equal to $Ne^2/m\epsilon_o c^2$, in which N is the number density of absorbers, e is the charge on an electron, m is the mass of an electron, $\epsilon_o$ is the permittivity, and c is the speed of light; wherein $\nu_j$ is the resonant absorption frequency; wherein $f_j$ is the oscillator strength; and wherein g is the transition probability; and by minimizing the sum, over all values of k, of the expression $[R_{data}(\nu_k) - R(\nu_k)]^2$, with respect to $A_j$, wherein $A_j$ represents oscillator peak amplitude equal to $\nu_{pj}^2 f_j / g_j \nu_j$, t is the number of data points to fit, k represents integers from 1 to t, $R_{data}$ is the measured value of reflectance, and the calculated reflectance R is simulated from the $A_j$ value.

10. The method of claim 9 wherein said sum of said expression is minimized by the iterative solution method represented by the equation:

$$\begin{bmatrix} \delta R/\delta A_1(\nu_1) & \delta R/\delta A_2(\nu_1) & \ldots & \delta R/\delta A_s(\nu_1) \\ \delta R/\delta A_1(\nu_2) & \delta R/\delta A_2(\nu_2) & \ldots & \delta R/\delta A_s(\nu_1) \\ \vdots & & & \\ \delta R/\delta A_1(\nu_t) & \delta R/\delta A_2(\nu_t) & \ldots & \delta R/\delta A_s(\nu_t) \end{bmatrix} \begin{bmatrix} \Delta A_1 \\ \Delta A_2 \\ \vdots \\ \Delta A_s \end{bmatrix} = \\ = \begin{bmatrix} R_{data}(\nu_1) - R(\nu_1) \\ R_{data}(\nu_2) - R(\nu_2) \\ \vdots \\ R_{data}(\nu_t) - R(\nu_t) \end{bmatrix}$$

wherein $\Delta A$ is an estimated correction to A.

11. The method of claim 1 wherein said step (b) is carried out in the presence of ambient gases, and including the additional steps of identifying features of said reflectance measured in said step (d) that are attributable to absorbance of radiation by said ambient gases, and subtracting said features from said measured reflectance.

12. The method of claim 11 including the additional step of determining the temperature of said ambient gases from said reflectance measured in said step (d).

13. The method of claim 5 wherein spectral radiance is measured in said step (e), and wherein said method serves to simultaneously determine, at said instants, the spectral emittance, temperature, thickness, and composition of said surface portion, as modified.

14. The method of claim 13 wherein said method serves to additionally determine, at said instants, the temperature and composition of said ambient gases.

15. The method of claim 1 additionally including the step of controlling said treating step (b) based upon said determined temperature and optical constants.

16. The method of claim 1 wherein said oscillators are spaced at equal intervals across said portion of said selected spectral range.

17. The method of claim 16 wherein said selected number s has a value of at least ten.

18. A method for fabricating an article, comprising the steps:
(a) providing a substrate having a surface;
(b) treating at least a portion of said surface for a certain period of time to effect modification thereof, accompanied by the formation of ambient gases and optionally by developing a film of material thereon, and carrying out the following steps in connection with said surface portion, as so modified;
(c) substantially continuously throughout said period causing electromagnetic radiation of frequencies v throughout a selected spectral range to impinge upon said surface portion at a selected angle of incidence;
(d) substantially continuously throughout said period measuring, at substantially the specular angle, spectral reflectance of said radiation from said surface portion, as a function of frequency;
(e) substantially continuously throughout said period measuring the radiance of said surface portion at least at one selected wavelength;
(f) determining, from the reflectance and radiance data obtained in said steps (d) and (e), the temperature T of said surface portion at selected instants during said period of time;
(g) determining optical constants for said surface portion at said instants by (1) selecting values for said optical constants utilizing a selection scheme in which the imaginary component of the optical constant expression is represented by a selected number of oscillators spaced across at least a portion of said selected spectral range, s having a value of at least two; (2) calculating reflectance based upon said angle of incidence, said selected values for said optical constants, and the thickness of any film of material that may be developed upon said substrate surface in said step (b); (3) comparing said calculated reflectance to the value of said reflectance measured in said step (d); and (4) iteratively adjusting said selected values of optical constants and comparing said calculated reflectance and measured reflectance value until said calculated reflectance substantially equals said measured value;
(h) identifying features of said reflectance measured in said step (d) that are attributable to absorbance of radiation by said ambient gases, and subtracting said features from said measured reflectance; and
(i) controlling said treating step (b) based upon said determined temperature and optical constants.

19. Apparatus for the in situ analysis of an article during processing, comprising:
(a) means for producing electromagnetic radiation of frequencies v throughout a selected spectral range, and for causing such radiation to impinge at a selected angle of incidence upon the surface of a substrate supported in a position proximate said apparatus;
(b) means for continuously measuring, as a function of frequency, specular reflectance of such impinging radiation from the surface of the substrate so supported, and for storing data so obtained;
(c) means for continuously measuring, at least at one selected wavelength, the radiance of the surface of the substrate so supported, and for storing data so obtained; and
(d) electronic data processing means programmed and operatively connected for processing reflectance and radiance data obtained by said means for measuring to determine, at any instant, the temperature of and the optical constants for the substrate surface, said optical constants being determined by (1) selecting values for said optical constants utilizing a selection scheme in which the imaginary component of the optical constant expression is represented by a selected number s of oscillators spaced across said selected spectral range, s having a value of at least two; (2) calculating reflectance based upon said angle of incidence, said selected values for said optical constants, and the thickness of any film of material that may be developed upon said substrate surface; (3) comparing said calculated reflectance to the value of said reflectance measured in said step (b), and (4) iteratively adjusting said selected values of optical constants and comparing said calculated reflectance and measured reflectance value until said calculated reflectance substantially equals said measured value.

20. The apparatus of claim 19 wherein said means for producing, both of said means for measuring, and said data processing means comprise a single instrument.

21. The apparatus of claim 20 wherein said instrument comprises an FT-IR spectrometer.

22. The apparatus of claim 19 wherein said selected spectral range of said means for producing is the infrared range, and wherein said data processing means is programmed to determine the complex dielectric function of the substrate surface, and the real and imaginary components thereof, represented respectively by the terms of the equation $$\epsilon(v) = \epsilon_r(v) + i\epsilon_i(v).$$

23. The apparatus of claim 22 wherein said oscillators are spaced at equal intervals across said portion of said selected spectral range; wherein said data processing means is programmed to determine said optical constants by application of the equation:

$$\epsilon(v) = \epsilon_\infty + \Sigma_j \frac{v_{pj}^2 f_j}{v_j^2 - v^2 - ig_j v}$$

wherein $\epsilon(v)$ is the complex dielectric function; wherein $\epsilon_\infty$ is the dielectric constant in the visible region of the spectrum; wherein j represents integers from 1 to s; wherein, in each of the summed oscillators of index j, constituting the imaginary part of the dielectric function, $v_p^2$ is the square of the plasma frequency, equal to $Ne^2/m\epsilon_o c^2$, in which N is the number density of absorbers, e is the charge on an electron, m is the mass of an electron, $\epsilon_o$ is the permittivity, and c is the speed of light; wherein $v_j$ is the resonant absorption frequency; wherein $f_j$ is the oscillator strength; and wherein g is the transition probability; and by minimizing the sum, over all values of k, of the expression $[R_{data}(v_k) - R(v_k)]^2$, with respect to $A_j$, wherein $A_j$ represents oscillator peak amplitude, equal to $v_{pj}^2 f_j / g_j v_j$, t is the number of data points to fit, k represents integers from 1 to t, $R_{data}$ is the measured value of reflectance, and the calculated reflectance R is simulated from the $A_j$ value.

24. The apparatus of claim 19 wherein said data processing means is programmed to identify features of the measured reflectance that are attributable to absorbance of radiation by ambient gases, and for subtracting the value of such features from the measured radiance values, and wherein said data processing means is additionally programmed to determine the temperature of the ambient gases from the measured reflectance.

25. The apparatus of claim 19 wherein said apparatus additionally includes means (e) for continuously measuring, as a function of frequency, specular transmittance of such impinging radiation through the substrate so supported, and for storing data so obtained; and wherein said data processing means is programmed to determine the temperature T of the substrate surface by determining the reflectance $R_o$ at one selected wavelength, as measured by said means (b) for measuring reflectance, determining the transmittance $t_o$ of the one selected wavelength, as measured by said means (e) for measuring transmittance, using the values so determined to determine the fraction $a_o$ of impinging radiation, of the one selected wavelength, that is absorbed by the sample, by application of the equation:

$$a_o = 1 - R_o - t_o,$$

and thereby determining the spectral emittance $e_o$ of the sample at the one selected wavelength, by the equation:

$e_o = a_o$; and matching the quantity $E_o/e_o$ to the spectral radiance $B_O(T)$ of a theoretical black body at the selected wavelength, to determine T in accordance with the relationship:

$$E_o/e_o = B_O(T),$$

wherein $E_o$ represents the one selected wavelength of radiance measured by said means (c) for measuring radiance.

26. The apparatus of claim 25 wherein said data processing means is programmed to determine the spectral emittance $e_\nu$ of the substrate surface over the selected spectral range of such impinging radiation, by the relationships:

$$a_\nu = 1 - R_\nu - t_\nu; \text{ and } e_\nu = a_\nu; \tag{1}$$

or $$e_\nu = E_\nu / B_\nu(T), \tag{2}$$

wherein $a_\nu$ represents sectral absorbance, and $R_\nu$ and $t_\nu$ are the spectral reflectance and transmittance measured by the respective means (b) and (e) for measuring, and wherein $E_\nu$ and $B_\nu(T)$ are, respectively, spectral radiance measured by said means (c) for measuring, and the spectral radiance of a theoretical black body at temperature T, both taken over the selected spectral range.

27. The apparatus of claim 19 wherein said data processing means is programmed and operatively connected for generating an electrical signal indicative of the temperature and optical constants of said substrate surface so determined; and wherein said apparatus additionally includes controllable means (f) for treating the surface of a substrate, so supported, for effecting modification thereof, and means (g) for controlling said means for treating so as to vary the conditions produced thereby, said means for controlling being operatively connected to said data processing means and being responsive to the electrical signal generated thereby.

* * * * *

UNITED STATES PATENT AND TRADEMARK OFFICE
CERTIFICATE OF CORRECTION

PATENT NO. : 5,403,433
DATED : April 4, 1995
INVENTOR(S) : Philip W. Morrison, et al It is certified that error appears in the above-indentified patent and that said Letters Patent is hereby corrected as shown below:

Column 5, line 45, column 6, line 57, column 10, line 10, column 14, line 3 (Claim 9), and column 16, line 50 (Claim 23), in all instances "$v^2_{pj}f_j$" should be --$v_{pj}^2 f_j$--.

Column 14, line 11 (Claim 9), "$v^{p2}$" should be --$v_p^2$--.

Column 6, line 5, and column 14, line 30 (Claim 10), after "$v_2$", first occurrence, add a parenthesis --)--; "$v_1$" should be --$v_2$--.

Column 15, line 37 (Claim 18), insert after "number" the letter --s--.

Column 17, line 33 (Claim 25), the provision beginning with the word "matching" should begin at the margin and be present in full size type.

Column 18, line 17 (Claim 26), "sectral" should be --spectral--.

Signed and Sealed this

Fifth Day of September, 1995

*Attest:*

BRUCE LEHMAN

*Attesting Officer*  *Commissioner of Patents and Trademarks*